United States Patent
Wang et al.

(10) Patent No.: US 6,939,321 B2
(45) Date of Patent: Sep. 6, 2005

(54) CATHETER BALLOON HAVING IMPROVED BALLOON BONDING

(75) Inventors: Edwin Wang, Tustin, CA (US); Florencia Lim, Union City, CA (US); Huong Chung, San Jose, CA (US); Chi Le Long, San Jose, CA (US); Nadine Ding, San Jose, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 261 days.

(21) Appl. No.: 10/255,487

(22) Filed: Sep. 26, 2002

(65) Prior Publication Data

US 2004/0062890 A1 Apr. 1, 2004

(51) Int. Cl.[7] ............... A61M 31/00; A61M 37/00; A61M 29/00; A61F 2/06
(52) U.S. Cl. ............ 604/103.08; 604/103; 604/103.05; 606/194; 623/1.11
(58) Field of Search ................. 604/93.01, 96.01, 604/101.01, 101.02, 103, 103.05, 103.06, 103.07, 103.08, 103.09, 103.11, 103.12, 104, 264, 523, 524, 915, 916, 919; 606/192, 194; 623/1.11, 1.12; 216/9, 10, 58, 67, 83, 95

(56) References Cited

U.S. PATENT DOCUMENTS

| | | | |
|---|---|---|---|
| 4,743,327 A | 5/1988 | DeHaan et al. | |
| 4,946,903 A | 8/1990 | Gardella, Jr. et al. | |
| 4,948,628 A | 8/1990 | Montgomery et al. | |
| 5,061,738 A | 10/1991 | Solomon et al. | |
| 5,118,524 A | 6/1992 | Thompson et al. | |
| 5,195,969 A | 3/1993 | Wang et al. | |
| 5,290,306 A | 3/1994 | Trotta et al. | |
| 5,314,562 A | 5/1994 | McDonnell et al. | |
| 5,437,900 A | 8/1995 | Kuzowski | |
| 5,462,781 A | 10/1995 | Zukowski | |
| 5,749,852 A * | 5/1998 | Schwab et al. | 604/103.1 |
| 5,868,704 A | 2/1999 | Campbell et al. | |
| 5,891,114 A | 4/1999 | Chien et al. | |
| 5,932,299 A | 8/1999 | Katoot | |
| 6,120,477 A | 9/2000 | Campbell et al. | |
| 6,139,525 A | 10/2000 | Davis-Lemessy et al. | |
| 6,428,506 B1 | 8/2002 | Simhambhatla et al. | |
| 2001/0011178 A1 | 8/2001 | Tomaschko et al. | |
| 2001/0032008 A1 | 10/2001 | Wang et al. | |
| 2003/0180488 A1 | 9/2003 | Lim et al. | |

FOREIGN PATENT DOCUMENTS

| | | |
|---|---|---|
| EP | 0 569 263 A2 | 11/1993 |
| EP | 0 592 320 A2 | 4/1994 |
| WO | WO 95/05555 | 2/1995 |

* cited by examiner

*Primary Examiner*—Brian L. Casler
*Assistant Examiner*—Mark K. Han
(74) *Attorney, Agent, or Firm*—Fulwider Patton Lee & Utecht LLP

(57) ABSTRACT

A balloon catheter and a method of making the balloon catheter, having a balloon which is bonded to an elongated shaft, and which has a first layer and a second layer and an improved strong bond between the balloon and the shaft. One aspect of the invention is directed to a balloon in which the balloon first layer has at least a section with a gas plasma-etched or chemical solution-etched surface for improved bondability. Another aspect of the invention is directed to a balloon in which the balloon first layer has a proximal end section bonded to an outer surface of the shaft and the balloon second layer has a proximal end section bonded to an inner surface of the shaft, and, in one embodiment, at least a section of the balloon first layer has a gas plasma-etched or chemical solution-etched surface.

38 Claims, 3 Drawing Sheets

CATHETER BALLOON HAVING IMPROVED BALLOON BONDING

BACKGROUND OF THE INVENTION

This invention generally relates to medical devices, and particularly to intracorporeal devices for therapeutic or diagnostic uses, such as balloon catheters. In percutaneous transluminal coronary angioplasty (PTCA) procedures, a guiding catheter is advanced until the distal tip of the guiding catheter is seated in the ostium of a desired coronary artery. A guidewire, positioned within an inner lumen of a dilatation catheter, is first advanced out of the distal end of the guiding catheter into the patient's coronary artery until the distal end of the guidewire crosses a lesion to be dilated. Then the dilatation catheter having an inflatable balloon on the distal portion thereof is advanced into the patient's coronary anatomy, over the previously introduced guidewire, until the balloon of the dilatation catheter is properly positioned across the lesion. Once properly positioned, the dilatation balloon is inflated with fluid one or more times to a predetermined size at relatively high pressures (e.g. greater than 8 atmospheres) so that the stenosis is compressed against the arterial wall and the wall expanded to open up the passageway. Generally, the inflated diameter of the balloon is approximately the same diameter as the native diameter of the body lumen being dilated so as to complete the dilatation but not overexpand the artery wall. Substantial, uncontrolled expansion of the balloon against the vessel wall can cause trauma to the vessel wall. After the balloon is finally deflated, blood flow resumes through the dilated artery and the dilatation catheter can be removed therefrom.

In such angioplasty procedures, there may be restenosis of the artery, i.e. reformation of the arterial blockage, which necessitates either another angioplasty procedure, or some other method of repairing or strengthening the dilated area. To reduce the restenosis rate and to strengthen the dilated area, physicians frequently implant a stent inside the artery at the site of the lesion. Stents may also be used to repair vessels having an intimal flap or dissection or to generally strengthen a weakened section of a vessel. Stents are usually delivered to a desired location within a coronary artery in a contracted condition on a balloon of a catheter which is similar in many respects to a balloon angioplasty catheter, and expanded to a larger diameter by expansion of the balloon. The balloon is deflated to remove the catheter and the stent left in place within the artery at the site of the dilated lesion. Stent covers on an inner or an outer surface of the stent have been used in, for example, the treatment of pseudo-aneurysms and perforated arteries, and to prevent prolapse of plaque. Similarly, vascular grafts comprising cylindrical tubes made from tissue or synthetic materials such as polyester, expanded polytetrafluoroethylene, and DACRON may be implanted in vessels to strengthen or repair the vessel, or used in an anastomosis procedure to connect vessels segments together.

In the design of catheter balloons, characteristics such as strength, compliance, and profile of the balloon are carefully tailored depending on the desired use of the balloon catheter, and the balloon material and manufacturing procedure are chosen to provide the desired balloon characteristics. A variety of polymeric materials are conventionally used in catheter balloons. Use of polymeric materials such as PET that do not stretch appreciably consequently necessitates that the balloon is formed by blow molding, and the deflated blow molded balloon forms wings which are folded around the catheter shaft prior to inflation of the balloon in the patient's body lumen. However, it can be desirable to employ balloons, referred to as formed-in-place balloons, that are not folded prior to inflation, but which are instead expanded to the working diameter within the patient's body lumen from a generally cylindrical or tubular shape (i.e., essentially no wings) that conforms to the catheter shaft.

A catheter balloon formed of expanded polytetrafluoroethylene (ePTFE) has been suggested. ePTFE is PTFE which has been expanded to form porous ePTFE which typically has a node and fibril microstructure comprising nodes interconnected by fibrils. However, ePTFE has proven difficult to bond to balloon liner materials and/or to catheter shafts.

It would be a significant advance to provide a catheter balloon, or other medical device component, with improved performance and bondability.

SUMMARY OF THE INVENTION

This invention is directed to a balloon catheter and a method of making the balloon catheter, having a balloon which is bonded to an elongated shaft, and which has a first layer and a second layer and an improved strong bond between the balloon and the shaft. One aspect of the invention is directed to a balloon in which the balloon first layer has at least a section with a gas plasma-etched or chemical solution-etched surface. The etched surface improves the strength of the bond between the first layer and the second layer and/or the catheter shaft. Another aspect of the invention is directed to a balloon in which the balloon first layer has a proximal end section bonded to an outer surface of the shaft and the balloon second layer has a proximal end section bonded to an inner surface of the shaft, and, in one embodiment, at least a section of the balloon first layer has a gas plasma-etched or chemical solution-etched surface.

A balloon catheter of the invention generally comprises an elongated shaft having a proximal end, a distal end, and at least one lumen, and a balloon on a distal shaft section with an interior in fluid communication with the at least one lumen of the shaft. The balloon has a proximal skirt section bonded to the shaft, a distal skirt section bonded to the shaft, an inflatable section therebetween, and first and second layers extending from the proximal skirt section to the distal skirt section. In a presently preferred embodiment, the first layer is an outer layer relative to the second layer, although the first layer may alternatively be an inner layer relative to the second layer. In one embodiment, the outer (e.g., first) layer extends beyond the ends of the inner (e.g., second) layer. Specifically, in one embodiment, the first layer has a proximal end section and a distal end section, which extend beyond the second layer of the balloon and onto the shaft, so that the proximal and distal end sections of the first layer are in contact with and bonded to the shaft. The catheter shaft typically comprises an outer tubular member defining the inflation lumen, and an inner tubular member defining a guidewire lumen extending at least within a distal shaft section, with the balloon proximal skirt section bonded to a distal portion of the outer tubular member and the balloon distal skirt section bonded to a distal portion of the inner tubular member. However, a variety of suitable catheter configurations can be used as are conventionally known, including dual lumen designs. The balloon catheter can be an over-the-wire type catheter with an guidewire lumen extending from the proximal to the distal end of the catheter, or alternatively a rapid exchange type catheter with a distal guidewire port in a distal end of the catheter, a proximal guidewire port in a distal shaft section distal of the proximal end of the shaft and typically spaced a substantial distance from the proximal end of the catheter, and a short guidewire lumen extending between the proximal and distal guidewire ports in the distal section of the catheter. A balloon catheter of the invention can be configured for use in a variety of applications including coronary and peripheral dilatation, stent delivery, drug delivery, and the like.

In a presently preferred embodiment, the first layer comprises expanded polytetrafluoroethylene (ePTFE), although a variety of suitable materials may be used including a porous polymeric material which in one embodiment is selected from the group consisting of expanded polytetrafluoroethylene (ePTFE), an ultra high molecular weight polyolefin such as ultra high molecular weight polyethylene, porous polyethylene, porous polypropylene, and porous polyurethane. In one embodiment, the porous material has a node and fibril microstructure. The node and fibril microstructure, when present, is produced in the material using conventional methods. ePTFE and ultra high molecular weight polyethylene (also referred to as "expanded ultra high molecular weight polyethylene") typically have a node and fibril microstructure, and are not melt extrudable. However, a variety of suitable polymeric materials can be used in the method of the invention including conventional catheter balloon materials which are melt extrudable. Preferably, ePTFE is formed into a balloon layer by bonding wrapped layers of the polymeric material together to form a tubular member, and not by conventional balloon blow molding. Although discussed primarily in terms of the embodiment in which the first layer of the balloon comprises ePTFE, it should be understood that a variety of suitable polymers may be used for the first layer.

In one embodiment, the balloon first layer has at least a section with a gas plasma-etched or chemical solution-etched surface. The etched section of the first layer typically extends along at least a portion of the proximal skirt section, although the etched section of the first layer may extend along the distal skirt section or along both the proximal and distal skirt sections. In one embodiment the etched section extends along the entire length of an inner surface of the first layer from the proximal to the distal end thereof. In a presently preferred embodiment, the etched sections of the first layer extend along at least part of the inner surface of the end sections of the outer layer which are in contact with and bonded to the shaft. Additionally, at least a section, and preferably a proximal and/or a distal end section, of an outer surface of the first layer is etched in one embodiment. The etched outer surface of the first layer is typically bonded to another component of the catheter such as a sleeve member, which may be a polymeric sleeve or a metallic band, on the end section of the first layer. For example, in one embodiment, the balloon catheter includes a sleeve member which preferably provides a higher balloon seal rupture pressure (i.e., a high strength bond between the balloon and shaft), and which is bonded to the shaft and to a portion of an etched inner or an etched outer surface of the first layer.

The etched surface is the result of a chemical reaction between the polymeric material forming the first layer and the etching compound. For example, in the case of an ePTFE first layer and a sodium naphthalene etching solution, an activated form of sodium reacts with the ePTFE, resulting in the extraction of fluorine atoms from the surface of the ePTFE and the formation of a carbonaceous layer. The etched surface layer (e.g., carbonaceous layer) is compatible with many adhesives, and improves the adhesive or fusion bondability of the ePTFE. The etched surface of the balloon has an increased surface energy compared to the balloon surface prior to being etched, for improved bondability to an adjacent component of the catheter such as the catheter shaft. The etched surface is preferably heat fusion and/or adhesive bonded to an adjacent member. In one embodiment, a mechanical engagement between the etched surface and the shaft improves the strength and durability (i.e., fatigue resistance) of the bond, where, for example, an outer member is provided which clamps or crimps down onto the balloon at the location of the bond between the balloon and the shaft.

In a presently preferred embodiment, the first layer is chemical solution-etched, and is most preferably chemical solution-etched using a sodium naphthalene solution. The chemical solution-etching produces a carbonaceous surface, resulting from the removal of fluorine atoms, and introduces hydroxyl, carbonyl, and carboxyl functionalities on and beneath the surface of the polymer (e.g., ePTFE). The preferred sodium naphthalene solution etching provides a durable, effective surface treatment for enhancing bondability of the first layer, with an improved short processing duration. Unlike the gas plasma etching, the chemical solution etching (e.g., sodium naphthalene) produces an etched surface with an excellent shelf life of about 60 days, and without requiring moisture free storage. However, alternative solutions can be used including a sodium-ammonia complex in liquid ammonia, and sodium naphthalene complex in tetrahydrofuran, and alternative processes can be used including gas plasma-etching. The terminology "etch" used herein in relation to the embodiment involving a plasma gas treatment should be understood to refer generally to the modification of the polymer which results from the gas-plasma treatment. In one embodiment, the gas plasma etched/treated surface is formed using an ammonia plasma (e.g., treatment with ammonia anions by reaction in an ammonia gas filled plasma chamber). Alternative gases may be used in the gas plasma etching including argon, helium, hydrogen, oxygen, and air, in addition to or instead of the ammonia gas. The ammonia gas plasma etching provides an amine functionality on and beneath the surface of the first layer (e.g., the ePTFE layer) of the balloon, for improved bondability.

In a presently preferred embodiment, the etching extends within the wall of the first layer from the etched surface to a depth equal to less than the wall thickness of the first layer. The limited, controlled depth of the etching limits the decomposition of the first layer, to provide a first layer with improved high strength and bondability. The etching is controlled by limiting the time duration of the etching process as for example by quenching the chemical solution-etching solution to stop the reaction before it is complete, and/or by using a self-limiting etching reaction in the case of the chemical solution-etching. In a preferred embodiment, the etching extends only to a shallow depth beneath the surface of the first layer, so that the majority of the first layer is unaffected by the etching but the surface of the first layer is highly bondable. In one embodiment in which the first layer is etched using sodium naphthalene, the etching extends from the etched surface to a depth equal to about 0.2 to about 0.5% of a wall thickness of the first layer etched section (prior to inflation of the balloon). Specifically, in one embodiment, the first layer etched section, etched using sodium naphthalene, has a wall thickness of about 50 to about 150 microns (um), and the etching extends from the etched surface to a depth equal to about 60 to about 600 nanometers (nm). In another embodiment in which the first layer is etched using the ammonia plasma method, the etching extends from the etched surface to a depth equal to about 0.01 to about 0.04% of the wall thickness of the first layer etched section. Specifically, in one embodiment, the first layer etched section, etched using the ammonia plasma method, has a wall thickness of about 50 to about 150 microns, and the etching extends from the etched surface to a depth equal to about 5 to about 50 nanometers.

A method of making a balloon catheter which embodies features of the invention generally includes positioning a balloon having an inner layer and an outer layer over a distal section of a catheter shaft, the outer layer having an inner surface with at least a section gas plasma-etched or chemical solution-etched. The proximal and distal end sections of the balloon are then bonded to the shaft, as for example by heat fusion and/or adhesive bonding, to form the balloon catheter.

Another aspect of the invention is directed to a balloon catheter with a balloon having a first layer and a second layer, the balloon first layer having a proximal end section bonded to an outer surface of the shaft, and the balloon second layer having a proximal end section bonded to an inner surface of the shaft. Thus, the inner and outer layers of the balloon are split apart at the proximal end, with the shaft located between and bonded to the two layers separately for an improved strong bond. The first and second layers of the balloon typically have at least a section bonded together, so that at least a portion of the balloon first layer distal to the proximal section of the first layer is typically bonded to an outer surface of the second layer. In one embodiment, a proximal sleeve member is provided which is secured to the first layer and to the shaft at the proximal skirt section of the balloon. The proximal sleeve member preferably increases the bond strength of the proximal skirt section. In one embodiment, the first layer has at least a section with a gas plasma-etched or chemical solution-etched surface. For example, the inner surface of at least the proximal end section of the first layer bonded to the shaft is, in one embodiment, gas plasma-etched or chemical solution-etched. In one embodiment, the first layer outer surface, bonded to the proximal sleeve member, is gas plasma-etched or chemical solution-etched, as discussed above in relation to the first embodiment of the invention.

The balloon catheter of the invention has an improved bond between the balloon and the catheter shaft. In a first embodiment, the improved bond is due at least in part to an etched section of the first layer of the balloon. The etched section provides a strong bond between the etched surface and an adjacent catheter component, with improved manufacturability. In another embodiment, the balloon has an improved bond between the proximal skirt section of the balloon and the shaft, in which the inner and outer layers of the balloon are split apart at the proximal end, with the shaft located between and bonded to the two layers separately for an improved strong bond. These and other advantages of the invention will become more apparent from the following detailed description and accompanying exemplary figures.

DETAILED DESCRIPTION OF THE INVENTION

Figure 1:
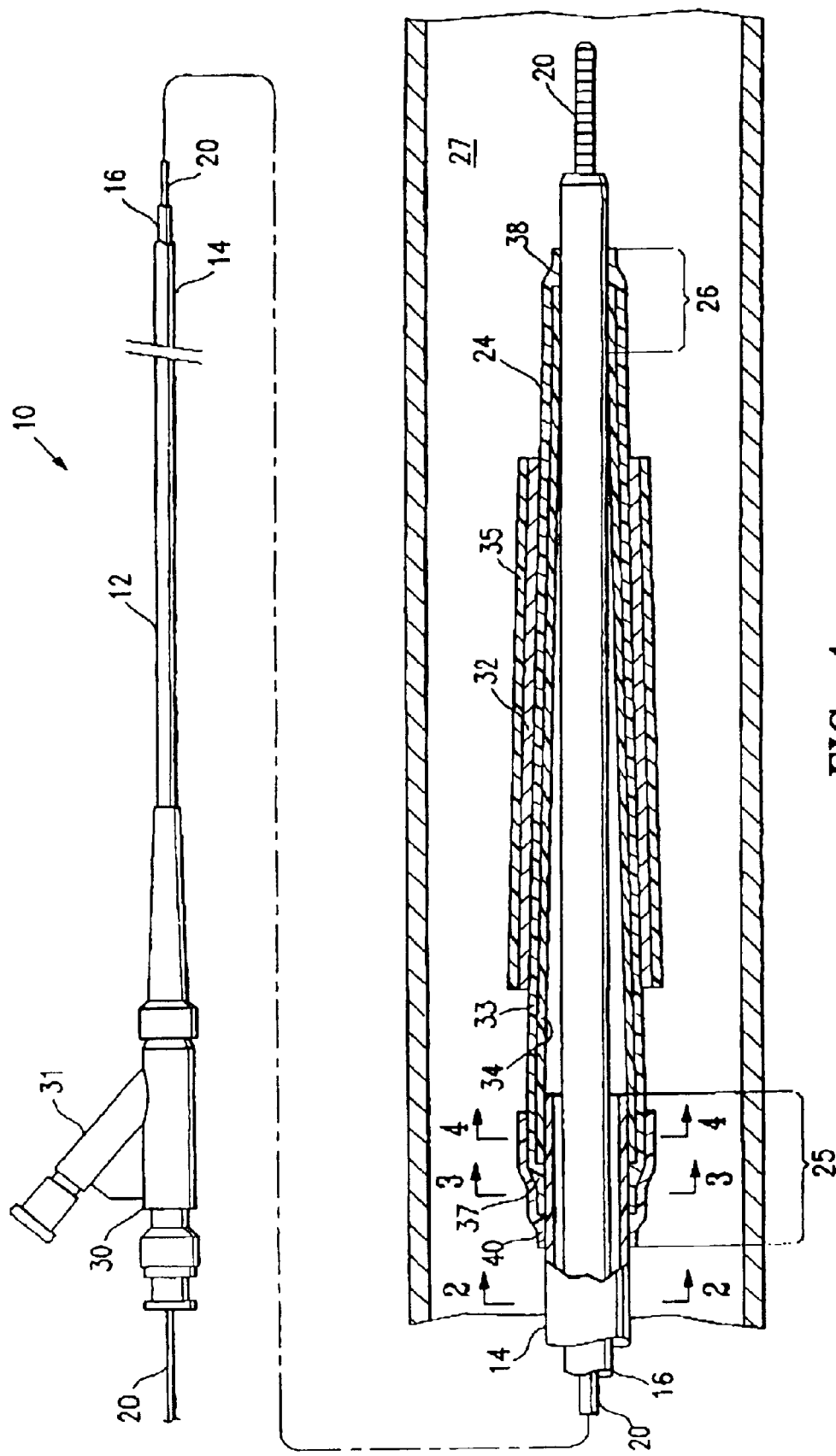
FIG. 1 is an elevational view, partially in section, of a stent delivery balloon catheter embodying features of the invention.
Figure 2:
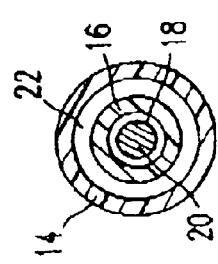
FIG. 2 is a transverse cross sectional view of the balloon catheter shown in FIG. 1, taken along line 2—2.
Figure 3:
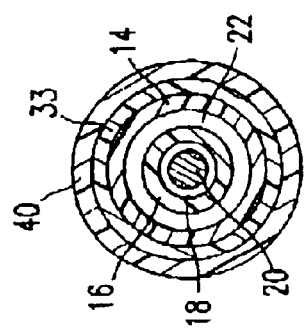
FIG. 3 is a transverse cross sectional view of the balloon catheter shown in FIG. 1, taken along line 3—3.
Figure 4:
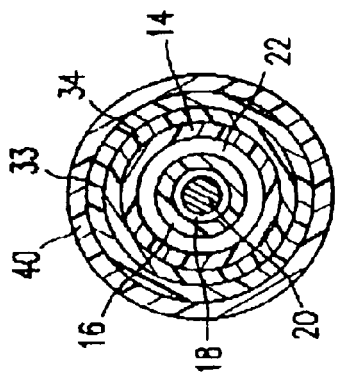
FIG. 4 is a transverse cross sectional view of the balloon catheter shown in FIG. 1, taken along line 4—4.
Figure 5:
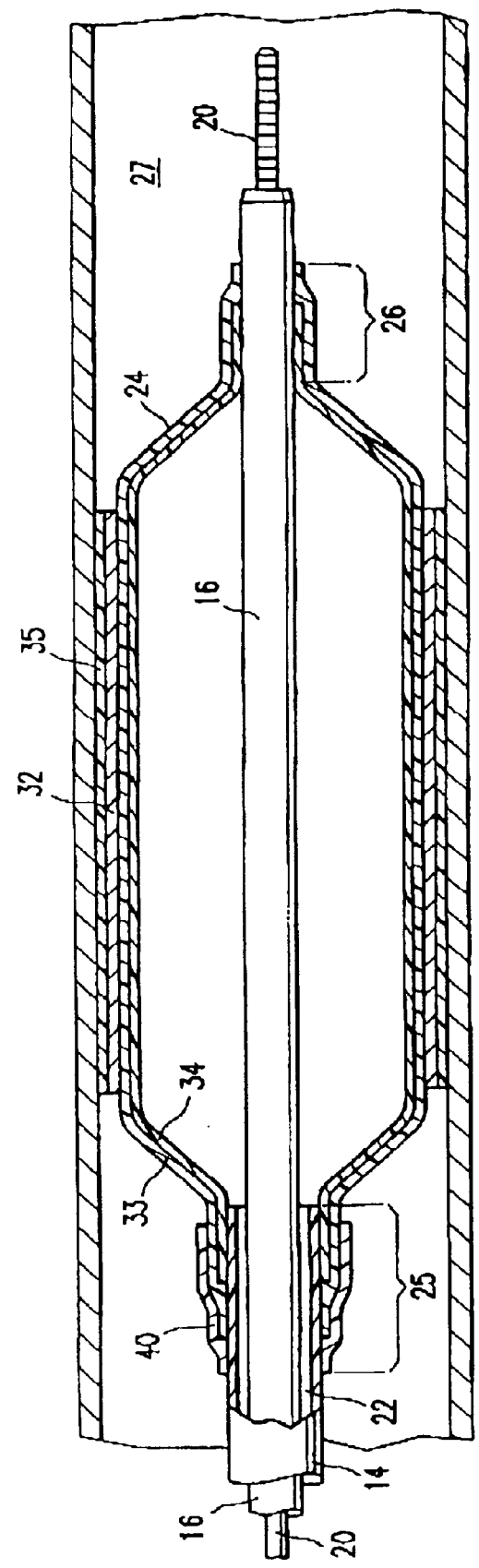
FIG. 5 illustrates the balloon catheter of FIG. 1, with the balloon in an inflated configuration to expand the stent within the patient's body lumen.

FIG. 1 illustrates an over-the-wire type stent delivery balloon catheter 10 embodying features of the invention. Catheter 10 generally comprises an elongated catheter shaft 12 having an outer tubular member 14 and an inner tubular member 16. Inner tubular member 16 defines a guidewire lumen 18 configured to slidingly receive a guidewire 20, and the coaxial relationship between outer tubular member 14 and inner tubular member 16 defines annular inflation lumen 22, as best shown in FIG. 2 illustrating a transverse cross section of the distal end of the catheter shown in FIG. 1, taken along line 2—2. An inflatable balloon 24 disposed on a distal section of catheter shaft 12 has a proximal skirt section 25 sealingly secured to the distal end of outer tubular member 14 and a distal skirt section 26 sealingly secured to the distal end of inner tubular member 16, so that the balloon interior is in fluid communication with inflation lumen 22. An adapter 30 at the proximal end of catheter shaft 12 is configured to provide access to guidewire lumen 18, and to direct inflation fluid through arm 31 into inflation lumen 22. In the embodiment illustrated in FIG. 1, the balloon 24 is illustrated prior to complete inflation thereof, with an expandable stent 32, with stent cover 35, mounted on the working length of the uninflated balloon 24 for implanting within a patient's body lumen 27. The distal end of catheter 10 may be advanced to a desired region of the patient's body lumen 27 in a conventional manner, the balloon 24 inflated to expand covered stent 32, and the balloon deflated, to implant the covered stent 32 in the body lumen 27.

Balloon 24 has an outer layer 33 and an inner layer 34, extending from the proximal skirt section 25 to the distal skirt section 26 of the balloon 24. The inner surface of the outer layer 33 is preferably bonded to the inner layer 34, as for example by fusion bonding or adhesive bonding. The balloon 24 is preferably bonded to the shaft 12 by fusion and/or adhesive bonding. Conventional adhesives such as light-cured (e.g., Dymax 204) and cyanoacrylates (e.g., Loctite 4011) may be used to bond layers 33, 34 to the shaft 12 at the proximal skirt section 25 and distal skirt section 26 of the balloon 24. In the embodiment illustrated in FIG. 1, the outer layer 33 of the balloon 24 has a proximal end section 37 proximal to the inner layer 34 and bonded to the outer tubular member 14, and a distal end section 38 distal to the inner layer 34 and bonded to the inner tubular member 16. The end sections 37,38 of the outer layer 33, together with end sections of the inner layer 34 bonded to the shaft 12, form the proximal and distal skirt sections 25, 26, respectively. The length of the sections of each layer 33 and 34 of the balloon 24 secured to the shaft to form the proximal and distal skirt sections 25, 26 are preferably minimized. Thus, the proximal and distal skirt sections 25, 26 preferably have a length about equal to the minimal length required to provide a suitably strong bond between the balloon 24 and the shaft 12. The proximal end section and the distal end section of the inner layer 34 bonded to the shaft have a length of typically about 1 to about 5 mm, and the proximal end section and the distal end section of the outer layer 33 extending beyond the inner layer 34 and bonded to the shaft have a length of typically about 1 mm to about 4 mm, preferably about 1 mm to about 2 mm, for a balloon 24 having a length of about 8 to about 60 mm and a nominal outer diameter of about 2 to about 18 mm. Although the proximal skirt section 25 is illustrated with a longer length than the distal skirt section, in alternative embodiments, the length of the skirt sections 25, 26 may be equal, or the proximal skirt section 25 may be shorter than the distal skirt section 26.

Additionally, in the embodiment of FIG. 1, a proximal outer sleeve member 40 has a distal portion bonded to an outer surface of the outer layer 33 and a proximal portion located proximal to the outer layer 33 and bonded to the outer tubular member 14. The sleeve member 40 preferably increases the rupture pressure of the bond between the balloon and shaft (and typically by at least about 100 psi), and preferably increases the fatigue resistance of the bond. In the embodiment of FIG. 1, the proximal sleeve member 40 comprises a polymeric material. The sleeve member 40 is preferably formed of polyurethanes, although it may be formed of a variety of suitable polymeric materials including polyamides such as nylon or polyether block amide (PEBAX), and may include radiopaque material incorporated into the polymeric matrix for use as a radiopaque marker for visualizing the catheter under fluoroscopy in the patient's body lumen. The sleeve member 40 is preferably bonded by fusion bonding, although it may alternatively be adhesively bonded. In alternative embodiments, a proximal sleeve member in the form of a metallic band (not shown) is mounted on at least a portion of the proximal skirt section 25 of the balloon 24. The metallic proximal sleeve member may be formed of a radiopaque material for use as a radiopaque marker, such as gold or a platinum-iridium alloy, or nonradiopaque materials. The metallic proximal sleeve member is typically crimped onto the outer surface of the outer layer 33 at the proximal skirt section, although it may alternatively be secured using an adhesive. The metallic proximal sleeve member reinforces the bond between the balloon and the shaft, to increase the durability of the bond after multiple inflations of the balloon. Thus, a metallic proximal sleeve member crimped onto the proximal skirt section 25 increased the durability of the bond to the shaft, so that the balloon can be inflated at the relatively high inflation pressure (i.e., 18 atm or more) multiple times without the proximal skirt section bond failing. For example, with the metallic sleeve member thereon, the proximal or distal skirt section 25, 26 typically does not fail before about 20 to about 50 inflations at the relatively high inflation pressure, whereas the skirt sections 25, 26 fail after about 1 to about 19 inflations in the absence of the metallic proximal sleeve member. Although not illustrated in FIG. 1, a distal sleeve member may be provided at the distal skirt section 26 of the balloon, similar to the polymeric or metallic proximal sleeve members discussed above.

In the embodiment of FIG. 1, the outer layer 33 of the balloon 24 has an inner surface which is gas plasma-etched or chemical solution-etched along at least a section of the length of the outer layer 33. In one embodiment, the etched section of the inner surface of the outer layer 33 extends along the entire length of the inner surface of the outer layer 33, to provide a secure bond to the shaft and to the inner layer 34. However, in alternative embodiments, the etched section of the inner surface of outer layer 33 extends along less than the entire length of the outer layer 33, and is therefore adjacent to a section of the inner surface of the outer layer 33 which is not etched. For example, in one embodiment the etched sections of the inner surface of the outer layer 33 extend along the proximal and distal skirt sections 25, 26 (i.e., along the sections of the outer layer 33 which are bonded to the shaft and which are bonded to the end sections of the inner layer bonded to the shaft). The length of each etched section of the inner surface of the outer layer 33 is typically about 50 to about 100% of the length of the outer layer 33, specifically about 60 to about 90% for a balloon length of about 8 to about 60 mm.

In a presently preferred embodiment, at least a section of the outer surface of the outer layer 33 of the balloon 24 is gas plasma-etched or chemical solution-etched, and preferably the etched section is a proximal section of the outer layer 33 which is bonded to the proximal sleeve member 40. Additionally, an outer surface of a distal portion of the outer layer 33 may similarly be etched in the embodiment in which including a distal sleeve member or other component such as a radiopaque marker on the outer surface of the outer layer 33 at the balloon distal skirt section 26. Preferably, the outer surface of the central, inflatable section of the outer layer 33 (having the stent 32 thereon in FIG. 1) is not etched, and the etched outer surface of the outer layer 33 is thus typically adjacent to a section of the outer surface of the outer layer 33 which is not etched. In a presently preferred embodiment, the etched section(s) of the outer surface of the outer layer 33 have a combined length which is less than the length of the section of the outer layer which is not etched. The proximal etched section of the outer surface of the outer layer 33, having at least a portion bonded to proximal sleeve member 40, is typically about 1 to about 2 mm in length for a balloon having a working length of about 8 to about 60 mm, and is typically about 2% to about 25% of the length of the outer layer 33.

The etching of the etched inner surface of the outer layer 33 preferably extends from the inner surface of the outer layer to a depth of about 0.04 to about 1.2% of a wall thickness of the outer layer 33 (prior to inflation of the balloon). Specifically, in one embodiment, the outer layer 33 has a wall thickness of about 50 to about 150 microns, and the etching of the etched inner surface of the outer layer 33 extends from the inner surface of the outer layer 33 to a depth of about 500 to about 600 nanometers. The etching of the outer surface of the outer layer 33 typically has about the same depth as the etching of the inner surface of the outer layer 33. Thus, the etched outer surface of the outer layer 33 has a depth equal to about 0.04 to about 1.2% of the wall thickness of the outer layer 33 (prior to inflation of the balloon).

Figure 6:
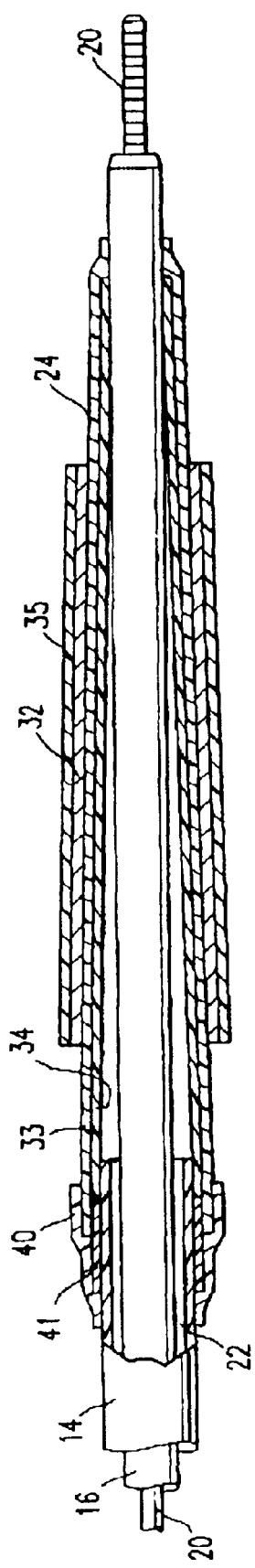
FIG. 6 illustrates an alternative embodiment of a balloon catheter embodying features of the invention, having an inner sleeve member between a proximal section of the outer layer of the balloon and the shaft outer tubular member, and an outer sleeve member.

In the embodiment of FIG. 1, the outer layer 33 and inner layer 34 of the balloon 24 are bonded directly to the outer tubular member 14 and the inner tubular member 16 of the shaft 12, without a separate polymer layer between the layers 33, 34 and the shaft 12. Alternatively, in one embodiment, a separate polymer member is used to facilitate bonding at least the inner layer 34 to the shaft 12. For example, FIG. 6 illustrates an alternative embodiment of the balloon catheter 10 of FIG. 1, in which an inner polymeric sleeve member 41 is bonded to the shaft between the balloon outer layer 33 and the outer tubular member 14. Inner sleeve 41 is typically the same as outer sleeve 40, apart from being bonded to an inner surface of outer layer 33, and preferably increases bond strength and fatigue resistance similar to outer sleeve 40. In one embodiment (not shown), outer polymeric sleeve member 40 is omitted and inner polymeric sleeve member 41 is bonded to the shaft between the balloon outer layer and the outer tubular member 14, providing similar bond strength as the embodiment of FIG. 1 having the outer sleeve member 40.

In a presently preferred embodiment, the etched inner and outer surfaces of the outer layer 33 are prepared using a sodium naphthalene etching solution. The outer layer 33 is etched by exposing the polymeric tube which forms the outer layer 33 to the sodium naphthalene solution, as for example by dipping the polymeric tube in a container of the sodium naphthalene solution. Sections of the polymeric tube may be masked to prevent etching of the sections before dipping the tube in the etching solution. For example, in order to prevent etching of all or part of the outer surface of the polymeric tube forming outer layer 33, a polymeric covering such as a polymeric sheath with a length equal to or less than the length of the polymeric tube, is placed on the polymeric tube, tightly fitting thereon, before the tube is dipped in the etching solution. The sheath prevents the etching solution from contacting the outer surface of the polymeric tube covered by the sheath. Similarly, a tightly fitting mandrel may be used in the inner lumen of the polymeric tube to mask sections of the inner surface of the polymeric tube. The duration of the tube in the etching solution is carefully controlled to limit the depth of the etching, although the etching solution reaction is typically a self-limiting reaction. After removal from the etching solution, the polymeric tube is typically dipped or otherwise rinsed in a solution such as isopropyl alcohol to quench/deactivate any remaining etching solution thereon. The quenching solution is then rinsed using warm water and the resulting etched tube is dried. For example, in one embodiment the ePTFE layer is etched using the following process. About 10–30 ml of about 10 to about 18 weight % Na-naphthalene in diethylene glycol dimethyl ether (2-methoxyethyl ether) solvent, available from Acton Technologies, Inc. under the trade name FluoroEtch Safety Solvent, is poured into a container and heated in a warm water bath (at about 37° C. or more). An ePTFE tube having a length of about 8 cm is tightly fit in a polymeric sheath (preferably formed of HDPE), and both ends are flared to facilitate the chemical solution flow therein. The entire sheathed ePTFE tube is dipped in the etch solution for about 45±15 seconds with constant agitation. About 10 sheathed ePTFE tubes may be treated at the same time using the same etch solution. The sheathed ePTFE tube is removed from the solution and drained for a minimum of about 5 seconds, and soaked in 20 ml of 100% isopropyl alcohol for about 5 to about 30 seconds at room temperature to deactivate the etch solution. The ePTFE tube is then washed in a warm water bath, which may be mildly acidic (not lower than pH 4), for about 1 minute. The acidity may be provided by acetic acid, to neutralize alkalinity of the etchant residue, provide fast effective cleaning, and contribute more acidic sites to the modified ePTFE surface for improved bonding to basic adhesives. The ePTFE tube is then air dried, or hot air dried at about 70° C. to about 75° C. for at least about 15 minutes.

In an alternative embodiment, the etched inner and outer surfaces of the outer layer 33 are prepared using ammonia gas plasma etching. The outer layer 33 is etched by placing a sheathed ePTFE tube in a plasma chamber. For example, in one embodiment, the plasma chamber has ammonia gas at a pressure of about 80 to about 90 mtorr. In a presently preferred embodiment, in addition to the reactive species formed by the ammonia, hydrogen gas ($H_2$) included in the chamber with the ammonia gas forms reactive species. The concentration of hydrogen is about 1% to about 50%. For example, in one embodiment, the plasma chamber has 99% ammonia, 1% hydrogen, at a pressure of about 86 mTorr. The ePTFE tube is exposed to the to ammonia plasma for about 1 to about 5 minutes, typically about 3 to 5 minutes to etch the ePTFE tube, with the ammonia plasma generated at a power of about 450 watts.

The thus etched tubular outer layer 33 of the balloon 24, formed of a porous polymeric material such as for example ePTFE, is positioned on an outer surface of the tubular inner layer 34, either before or after the inner layer 34 is bonded to the shaft (i.e., to the outer and inner tubular members 16, 14), and bonded to the shaft. For example, to form a fusion bond, heat is applied at the proximal and distal end sections of the inner tubular layer 34, to melt the polymeric material of the shaft 12 and the polymeric material of the inner tubular layer 34 at least at the interface thereof, and fusion bond the proximal and distal end sections of the inner tubular layer 34 of the balloon 24 to the outer and inner tubular members 14, 16, respectively. Specifically, the ends of the balloon, in position against the catheter shaft and typically with shrink tubing therearound, are heated to a temperature at or above the melting temperature of the polymers, and the polymeric material allowed to cool to form a fusion bond.

During a medical procedure, the balloon 24 is typically inflated to a working pressure of about 6 atm to about 25 atm, preferably about 6 atm to about 20 atm. The balloon is inflatable within the working pressure range without the skirt sections 25, 26 of the balloon 24 failing. In the embodiment of FIG. 1, the balloon 24 bonded to the shaft, and including proximal sleeve member 40, preferably has a rupture pressure at the proximal fusion/adhesive bond of at least about 210 psi, and more specifically of about 300 to about 400 psi.

Figure 8:
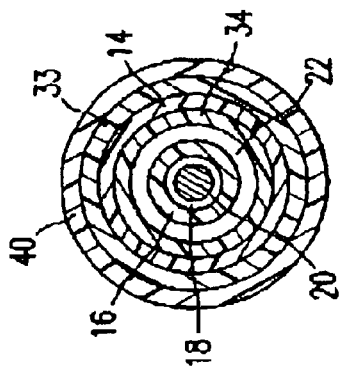
FIG. 8 is a transverse cross section of the catheter of FIG. 7, taken along line 8—8.
Figure 7:
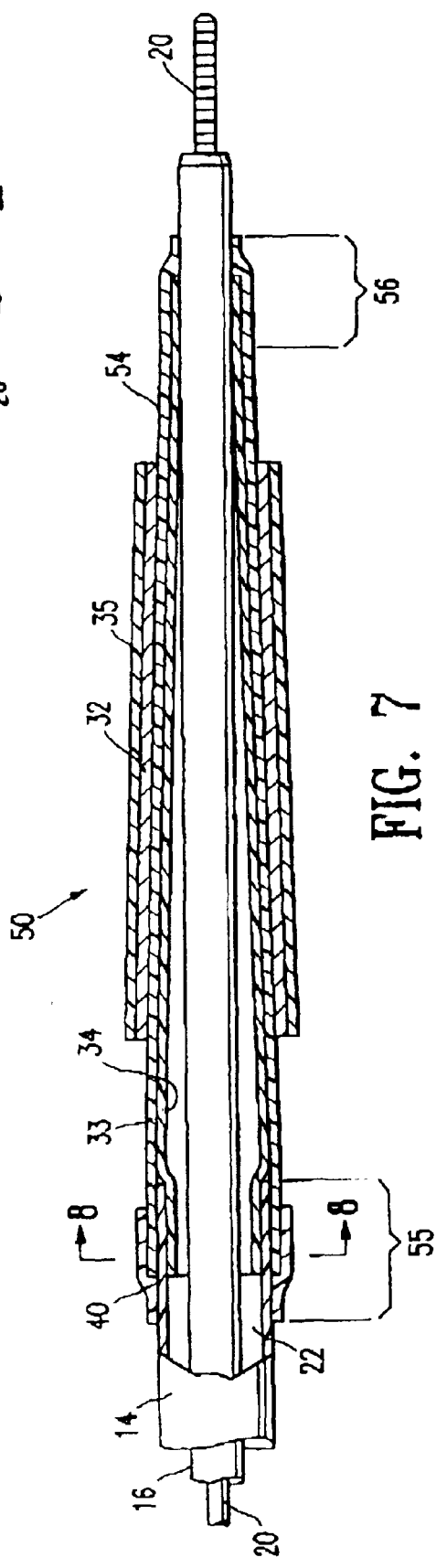
FIG. 7 illustrates an alternative embodiment of a balloon catheter embodying features of the invention, including a balloon having a first layer with a proximal end section bonded to an outer surface of the shaft, and a second layer with a proximal end section bonded to an inner surface of the shaft.

FIG. 7 illustrates an alternative aspect of the invention, directed to a balloon catheter 50 with a balloon 54 having a proximal shaft section 55 formed by bonding inner an outer layers 33, 34 of the balloon on either surface of the outer tubular member 14. The shaft and balloon components are typically the same as the corresponding components in the balloon catheter 10 of FIG. 1, and accordingly have the same reference numerals. The balloon 54 outer layer 33 has a proximal end section bonded to an outer surface of the outer tubular member 14, and the balloon inner layer 34 has a proximal section bonded to an inner surface of the shaft, to form the balloon proximal shaft section 55. Distal end of layers 33, 34 are bonded to the shaft inner tubular member 16, forming the distal skirt section 56 of the balloon 54. At proximal shaft section 55, the proximal end of balloon outer layer 33 is preferably fusion bonded to the shaft, but may be adhesively bonded thereto, and the proximal end of the inner layer 34 is preferably adhesively bonded to the outer tubular member 14. Although illustrated with the two layers 33,34 extending about the same length along the outer tubular member 14 in alternative embodiments (not shown), one of the layers 33, 34 may extend further distally along the outer tubular member 14. FIG. 8 is a transverse cross section of the catheter of FIG. 7, taken along line 8—8.

In the embodiment illustrated in FIG. 7, proximal sleeve member 40 is secured to the outer surface of the balloon outer layer 33. The proximal sleeve member 40 has a distal portion bonded to an outer surface of the outer layer 33 and a proximal portion bonded to the outer tubular member 14. The balloon 54 bonded to the shaft, and including proximal sleeve member 40, preferably has a rupture pressure at the proximal fusion/adhesive bond of at least about 210 psi, and more specifically of about 300 to about 400 psi.

In one embodiment of the catheter 50 illustrated in FIG. 7, the outer layer 33 has at least a section with an etched surface. In one embodiment, the inner surface of the outer layer 33 has an etched section extending along at least the portion of the outer layer 33 inner surface which is bonded to the outer tubular member 14. Similarly, in one embodiment, the outer surface of the outer layer 33 has an etched section extending along at least the portion of the outer layer 33 outer surface which is bonded to the proximal sleeve member 40. The discussion above relating to the etched surfaces of the outer layer 33 of the embodiment of FIG. 1 applies to the etched surface(s) of the embodiment of FIG. 7.

In a presently preferred embodiment, the balloon outer layer 33 of the balloon catheters 10, 50 comprises a porous polymeric material, and preferably a microporous polymeric material having a node and fibril microstructure, such as ePTFE, and the inner layer 34 is formed of a polymeric material preferably different from the polymeric material of the outer layer 33. Preferably, the length of outer layer 33 in contact with inner layer 34 is bonded thereto, and preferably by heat fusion bonding. Inner layer 34 limits or prevents leakage of inflation fluid through the microporous ePTFE to allow for inflation of the balloon 24, and is preferably an elastomeric material to facilitate deflation of the balloon 24 to a low profile deflated configuration. The inner layer 34 is preferably formed of an elastomeric material, including dienes, polyurethanes, silicone rubbers, polyamide block copolymers, and the like. The elastomeric material forming layer 34 may consist of a separate layer which neither fills the pores nor disturbs the node and fibril structure of the ePTFE layer 33, or it may at least partially fill the pores of the ePTFE layer 33.

The ePTFE layer 33 is formed according to conventional methods, in which a sheet of ePTFE polymeric material is wrapped with overlapping or abutting edges to form a tubular body and then heated to fuse the wrapped material together. The sheet of polymeric material preferably has the desired microstructure (e.g., porous and/or node and fibril) before being wrapped on the mandrel. The sheet of ePTFE polymeric material is wrapped spirally along a length of the mandrel, or by folding the sheet around the circumference of the mandrel so that the longitudinal edges of the sheet extend in a substantially straight line along the length of the mandrel, to form one or more layers, and preferably about two to about five layers, of wrapped material. The multiple layers of ePTFE are typically heated to fuse the layers together. The tube of ePTFE polymeric material is typically further processed by being stretched, sintered, compacted, and sintered again, to provide the desired properties such as the desired dimension, and dimensional stability (i.e., to minimize changes in length occurring during inflation of the balloon). The completed ePTFE layer 33 is then etched in accordance with the invention and bonded to or otherwise combined with elastomeric liner 34 either before or after layer 34 is bonded to the shaft.

The dimensions of catheters 10, 50 are determined largely by the size of the balloon and guidewire to be employed, the catheter type, and the size of the artery or other body lumen through which the catheter must pass or the size of the stent being delivered. Typically, the outer tubular member 14 has an outer diameter of about 0.025 to about 0.04 inch (0.064 to 0.10 cm), usually about 0.037 inch (0.094 cm), and the wall thickness of the outer tubular member 14 can vary from about 0.002 to about 0.008 inch (0.0051 to 0.02 cm), typically about 0.003 to 0.005 inch (0.0076 to 0.013 cm). The inner tubular member 16 typically has an inner diameter of about 0.01 to about 0.018 inch (0.025 to 0.046 cm), usually about 0.016 inch (0.04 cm), and a wall thickness of about 0.004 to about 0.008 inch (0.01 to 0.02 cm). The overall length of the catheter 10 may range from about 100 to about 150 cm, and is typically about 143 cm. Preferably, balloon 24 has a length about 0.8 cm to about 6 cm, and an inflated working diameter of about 2 to about 10 mm.

Inner tubular member 16 and outer tubular member 14 can be formed by conventional techniques, for example by extruding and necking materials already found useful in intravascular catheters such a polyethylene, polyvinyl chloride, polyesters, polyamides, polyimides, polyurethanes, and composite materials. The various components may be joined using conventional bonding methods such as by fusion bonding or use of adhesives. In the embodiment illustrated in FIG. 1, the outer and inner tubular members 14, 16 are each formed of a single-layered, uniform polymeric member. However, it should be understood that in alternative embodiments, one or both of the outer and inner tubular members 14, 16 may be a multilayered or blended polymeric member. Although the shaft is illustrated as having an inner and outer tubular member, a variety of suitable shaft configurations may be used including a dual lumen extruded shaft having a side-by-side lumens extruded therein. Similarly, although the embodiment illustrated in FIG. 1 is an over-the-wire stent delivery catheter, balloons of this invention may also be used with other types of intravascular catheters, such as rapid exchange type balloon catheters. While the present invention is described herein in terms of certain preferred embodiments, those skilled in the art will recognize that various modifications and improvements may be made to the invention without departing from the scope thereof. Moreover, although individual features of one embodiment of the invention may be discussed herein or shown in the drawings of the one embodiment and not in other embodiments, it should be apparent that individual features of one embodiment may be combined with one or more features of another embodiment or features from a plurality of embodiments.

What is claimed:

1. A balloon catheter, comprising:
   a) an elongated shaft having a proximal end, a distal end, and an inflation lumen; and
   b) a balloon on a distal shaft section, having an interior in fluid communication with the inflation lumen of the shaft, and having a proximal and a distal skirt section bonded to the shaft and an inflatable section therebetween, and a polymeric first layer and a polymeric second layer extending from the proximal skirt section to the distal skirt section, the first layer having an inner surface which has at least a section which is gas plasma-etched or chemical solution-etched and an outer surface which has at least a section which is gas plasma-etched or chemical solution-etched.

2. The balloon catheter of claim 1 wherein first layer of the balloon is a porous material selected from the group consisting of expanded polytetrafluoroethylene, ultra high molecular weight polyolefin, ultra high molecular weight polyethylene, porous polyethylene, porous polypropylene, and porous polyurethane.

3. The balloon catheter of claim 1 wherein the first layer of the balloon comprises expanded polytetrafluoroethylene.

4. The balloon catheter of claim 3 wherein the first layer of the balloon is an outer layer relative to the second layer of the balloon.

5. The balloon catheter of claim 1 wherein the etched section of the inner surface of the first layer extends along at least a portion of the proximal skirt section.

6. The balloon catheter of claim 5 wherein the first layer further includes a gas plasma-etched or chemical solution-etched distal section having a gas plasma-etched or chemical solution-etched surface and extending along at least a portion of the distal skirt section.

7. The balloon catheter of claim 1 wherein the etched section of the inner surface of the first layer extends along the entire length of an inner surface of the first layer from the proximal to the distal end thereof.

8. The balloon catheter of claim 7 wherein the etched section of the outer surface of the first layer is a proximal section adjacent to a section of the outer surface of the first layer which is not etched.

9. The balloon catheter of claim 1 wherein the etched section of the inner surface of the first layer has at least a portion bonded to the catheter shaft.

10. The balloon catheter of claim 1 wherein the second layer of the balloon comprises an elastomeric polymeric material bonded to the inner surface of the first layer.

11. The balloon catheter of claim 10 wherein the etched section of the inner surface of the first layer has at least a portion bonded to the elastomeric second layer of the balloon.

12. The balloon catheter of claim 1 wherein the etched sections of the inner and outer surfaces of the first layer are sodium naphthalene solution-etched.

13. The balloon catheter of claim 1 wherein the etched sections of the inner and outer surfaces of the first layer are ammonia gas plasma-etched.

14. The balloon catheter of claim 1 wherein the etching extends from the etched inner surface to a depth equal to about 0.2 to about 0.5% of a wall thickness of the first layer etched inner surface section.

15. The balloon catheter of claim 1 wherein the first layer etched inner surface section has a wall thickness of about 50 to about 150 micrometers, and the etching extends from the etched inner surface to a depth equal to about 0.2 to about 0.6 micrometers.

16. The balloon catheter of claim 1 wherein the first layer is on an outer surface of the second layer, and the etched section of the inner surface of the first layer extends along at least a proximal end section of the first layer bonded to the shaft.

17. The balloon catheter of claim 16 wherein the proximal end section of the first layer is proximal to the second layer and is bonded to an outer surface of the shaft.

18. The balloon catheter of claim 17 including a proximal sleeve member bonded to the shaft and bonded to an etched inner or an etched outer surface portion of at least part of the proximal end section of the first layer.

19. The balloon catheter of claim 18 wherein the proximal sleeve member has a distal portion bonded to the etched outer surface of the first layer and has a proximal portion proximal to the first layer and bonded to the shaft.

20. The balloon catheter of claim 18 wherein the proximal sleeve member comprises a polymeric material selected from the group consisting of polyurethanes and polyamides.

21. The balloon catheter of claim 16 wherein the proximal end section of the first layer is bonded to an outer surface of the shaft and a proximal end section of the second layer is bonded to an inner surface of the shaft.

22. The balloon catheter of claim 16 wherein the etched section of the outer surface of the first layer extends along at least the proximal end section of the first layer.

23. A balloon catheter, comprising:
   a) an elongated shaft having a proximal end, a distal end, and an inflation lumen; and
   b) a balloon on a distal shaft section, having an interior in fluid communication with the inflation lumen of the shaft, and having a proximal and a distal skirt section bonded to the shaft and an inflatable section therebetween, and a first and a second layer extending from the proximal skirt section to the distal skirt section, the proximal skirt section of the balloon being formed at least in part by a proximal end section of the first layer bonded to an outer surface of the shaft and a proximal end section of the second layer bonded to an inner surface of the shaft.

24. The balloon catheter of claim 23 wherein at least a distal section of the first layer, located distal to the proximal end section of the first layer, is bonded to an outer surface of the second layer.

25. The balloon catheter of claim 24 wherein the entire length of an inner surface of the first layer from the proximal to the distal end thereof is gas plasma-etched or chemical solution-etched.

26. The balloon catheter of claim 23 wherein the first layer of the balloon is a porous material selected from the group consisting of expanded polytetrafluoroethylene, ultra high molecular weight polyolefin, ultra high molecular weight polyethylene, porous polyethylene, porous polypropylene, and porous polyurethane.

27. The balloon catheter of claim 23 including a proximal sleeve member having a proximal portion proximal to the first layer and bonded to the shaft and a distal portion bonded to an outer surface of the first layer.

28. The balloon catheter of claim 27 wherein the first layer outer surface bonded to the proximal sleeve member is gas plasma-etched or chemical solution-etched.

29. The balloon catheter of claim 23 wherein the first layer has at least a section with a gas plasma-etched or chemical solution-etched surface.

30. The balloon catheter of claim 23 wherein the proximal end section of the first layer bonded to the shaft is gas plasma-etched or chemical solution-etched.

31. A balloon catheter, comprising:
   a) an elongated shaft having a proximal end, a distal end, and an inflation lumen; and
   b) a balloon on a distal shaft section, having an interior in fluid communication with the inflation lumen of the shaft, an outer layer, and an inner layer, and the outer layer has an inner surface which is chemical-solution etched along the entire length of the inner surface of the outer layer from the proximal to the distal end of the inner surface of the outer layer, and the outer layer has an outer surface with a chemical solution-etched proximal end section and a chemical-solution etched distal end section.

32. The balloon catheter of claim 31 including a metallic sleeve member on at least one of the chemical-solution etched end sections of the outer surface of the outer layer.

33. The balloon catheter of claim 31 including a polymeric sleeve member on the shaft, and which is bonded to a portion of the etched inner surface of the balloon outer layer.

34. A balloon catheter, comprising:
a) an elongated shaft having a proximal end, a distal end, and an inflation lumen; and
b) a balloon on a distal shaft section, having an interior in fluid communication with the inflation lumen of the shaft, and having a proximal and a distal skirt section bonded to the shaft and an inflatable section therebetween, and a first and a second layer extending from the proximal skirt section to the distal skirt section, the first layer having at least a section with a gas plasma-etched or chemical solution-etched surface, and the first layer is on an outer surface of the second layer, and the etched section of the first layer extends along at least a proximal end section of the first layer located proximal to the second layer and bonded to an outer surface of the shaft, and wherein a proximal sleeve member is bonded to the shaft and is bonded to an etched inner or an etched outer surface of at least part of the proximal end section of the first layer.

35. A balloon catheter, comprising:
a) an elongated shaft having a proximal end, a distal end, and an inflation lumen; and
b) a balloon on a distal shaft section, having an interior in fluid communication with the inflation lumen of the shaft, and having a proximal and a distal skirt section bonded to the shaft and an inflatable section therebetween, and a polymeric first layer and a polymeric second layer extending from the proximal skirt section to the distal skirt section, the first layer having at least a section with a gas plasma-etched or chemical solution-etched surface, and the first layer is on an outer surface of the second layer, and wherein a sleeve member is bonded to the shaft and is bonded to at least part of the etched section of the first layer.

36. The balloon catheter of claim 35 wherein the etched section of the first layer bonded to the sleeve member extends along an innersurface of the first layer.

37. The balloon catheter of claim 35 wherein the etched section of the first layer bonded to the sleeve member extends along an outer surface of the first layer.

38. A method of making a balloon catheter, comprising:
a) positioning a balloon having an inner layer and an outer layer over a distal section of a catheter shaft, the outer layer having an inner surface with at least a section gas plasma-etched or chemical solution-etched and an outer surface with at least a section gas plasma-etched or chemical solution-etched; and
b) bonding proximal and distal end sections of the balloon to the shaft to form the balloon catheter having at least a portion of the gas-plasma etched inner surface of the outer layer of the balloon bonded to the shaft or to the inner layer of the balloon.

* * * * *

UNITED STATES PATENT AND TRADEMARK OFFICE
CERTIFICATE OF CORRECTION

PATENT NO. : 6,939,321 B2
DATED : September 6, 2005
INVENTOR(S) : Edwin Wang et al.

It is certified that error appears in the above-identified patent and that said Letters Patent is hereby corrected as shown below:

Title page,
Item [75], Inventors, delete "Nadine" and insert -- Ni --.

Column 10,
Line 10, delete "to the to" and insert -- to the --.

Signed and Sealed this

Twenty-fourth Day of January, 2006

JON W. DUDAS
*Director of the United States Patent and Trademark Office*